(12) United States Patent
Ewell

(10) Patent No.: US 11,357,269 B2
(45) Date of Patent: Jun. 14, 2022

(54) MULTILAYER LINING FOR CLOTHING

(71) Applicant: EC BRAND COM IMP EXP DE VEST EM GERAL LTDA, Sorocaba (BR)

(72) Inventor: Emily Steed Ewell, Sorocaba (BR)

(73) Assignee: EC BRAND COM IMP EXP DE VEST EM GERAL LTDA, Sorocaba (BR)

( * ) Notice: Subject to any disclaimer, the term of this patent is extended or adjusted under 35 U.S.C. 154(b) by 47 days.

(21) Appl. No.: 16/496,231

(22) PCT Filed: Aug. 21, 2018

(86) PCT No.: PCT/BR2018/050295
§ 371 (c)(1),
(2) Date: Sep. 20, 2019

(87) PCT Pub. No.: WO2019/036783
PCT Pub. Date: Feb. 28, 2019

(65) Prior Publication Data
US 2020/0170309 A1    Jun. 4, 2020

(30) Foreign Application Priority Data

Aug. 22, 2017    (BR) ...................... 10 2017 017992 3

(51) Int. Cl.
*A41B 17/00*       (2006.01)
*A41D 31/30*       (2019.01)
(Continued)

(52) U.S. Cl.
CPC ............ *A41B 17/00* (2013.01); *A41D 31/145* (2019.02); *A41D 31/305* (2019.02); *A61F 13/00* (2013.01); *B32B 5/26* (2013.01); *B32B 27/12* (2013.01); *B32B 27/40* (2013.01); *A41B 2400/22* (2013.01); *A41B 2400/34* (2013.01); *A41B 2500/10* (2013.01);
(Continued)

(58) Field of Classification Search
CPC . A41B 17/00; A41B 2500/10; A41B 2400/22; A41B 2400/34; A41D 31/305; A41D 31/145; A61F 13/00
See application file for complete search history.

(56) References Cited

U.S. PATENT DOCUMENTS

| 4,214,319 A * | 7/1980 | Bollag ................. A41D 27/24 156/93 |
| 2009/0123700 A1* | 5/2009 | Conley ................ A41D 31/305 428/152 |

(Continued)

FOREIGN PATENT DOCUMENTS

| CN | 201286338 Y | 8/2009 |
| CN | 201444957 U | 5/2010 |

(Continued)

*Primary Examiner* — Jeremy R Pierce
(74) *Attorney, Agent, or Firm* — Hamre, Schumann, Mueller & Larson, P.C.

(57) ABSTRACT

The present disclosure relates to a breathable, reusable, leakproof, absorbent, antimicrobial, waterproof and vapor disperser multilayer lining for clothing. A purpose of this lining is to avoid the release of body fluids such as sweat, (Continued)

blood, vaginal fluids, menstrual fluid, urine, breast milk or postoperative fluids.

10 Claims, 1 Drawing Sheet

(51) Int. Cl.
  *A41D 31/14* (2019.01)
  *A61F 13/00* (2006.01)
  *B32B 27/12* (2006.01)
  *B32B 27/40* (2006.01)
  *B32B 5/26* (2006.01)
  *A61F 13/15* (2006.01)
  *A61F 13/47* (2006.01)

(52) U.S. Cl.
  CPC .............. *A61F 2013/00089* (2013.01); *A61F 2013/15016* (2013.01); *A61F 2013/15146* (2013.01); *A61F 2013/4708* (2013.01); *B32B 2255/02* (2013.01); *B32B 2262/14* (2013.01); *B32B 2307/718* (2013.01); *B32B 2307/724* (2013.01); *B32B 2307/7265* (2013.01); *B32B 2437/00* (2013.01); *D10B 2201/00* (2013.01); *D10B 2509/00* (2013.01)

(56) References Cited

U.S. PATENT DOCUMENTS

| | | |
|---|---|---|
| 2013/0006288 A1 | 1/2013 | Callas et al. |
| 2014/0039432 A1* | 2/2014 | Dunbar ............. A61F 13/15577 604/360 |
| 2017/0143059 A1* | 5/2017 | Gallagher ................. B32B 7/08 |
| 2018/0084845 A1* | 3/2018 | Cumiskey ............ A41D 31/185 |

FOREIGN PATENT DOCUMENTS

| | | |
|---|---|---|
| CN | 101906681 A | 12/2010 |
| CN | 102134776 A | 7/2011 |
| CN | 202396517 U | 8/2012 |
| CN | 103938361 A | 7/2014 |
| CN | 104862856 A | 8/2015 |
| CN | 105442325 A | 3/2016 |
| CN | 105803787 A | 7/2016 |
| CN | 106183210 A | 12/2016 |
| CN | 106240074 A | 12/2016 |
| FR | 2247199 A1 | 5/1975 |
| JP | H04197353 A | 7/1992 |
| JP | H08182699 A | 7/1996 |
| JP | H10165432 A | 6/1998 |
| JP | 2002085447 A | 3/2002 |
| JP | 2011135998 A | 7/2011 |
| KR | 101688837 B1 | 12/2016 |

* cited by examiner

MULTILAYER LINING FOR CLOTHING

CROSS-REFERENCE TO RELATED APPLICATIONS

This application is a national stage entry under 35 U.S.C. 371 of PCT Patent Application No. PCT/BR2018/050295, filed Aug. 21, 2018, which claims priority to Brazilian Patent Application No. 10 2017 017992 3, filed Aug. 22, 2017, the entire contents of each of which are incorporated herein by reference.

FIELD OF THE DISCLOSURE

The present disclosure is a multilayer breathable, reusable, leak-proof garment lining with absorbent, antimicrobial, waterproofing and vapor dispersion functions.

BACKGROUND OF THE DISCLOSURE

Clothes with features providing solutions for consumers are also able to increase their well-being and health. Currently, there are different solutions for issues related to the release of body fluids, such as sweat, blood, vaginal fluids, menstrual fluid, urine, breast milk or postoperative fluids.

Nonetheless, many of the existing solutions for the release of body fluids are not practical, for they entail everyday use and reapplication. Additionally, disposal after use may create further technical problems for consumers.

That said, washable and reusable products to solve problems regarding the release of body fluids are what the consumer wishes for. Furthermore, the high durability of such products is another welcomed feature.

The present disclosure relates to a breathable, reusable and leakproof multilayer lining for clothing. The purpose of this lining is mainly to avoid the release of body fluids such as sweat, blood, vaginal fluids, menstrual fluid, urine, breast milk or postoperative fluids. The lining may be sewn or pasted to the garment of choice in order to increase the quality of life and well-being of consumers. Said garments to which the lining may be applied are: men and women's underwear, shorts, Bermuda shorts, skirts, trousers, brassieres, shirts, t-shirts, overalls, panty girdles, dresses, women's and men's pajamas, and others.

This multilayer lining for clothing has a minimum of four layers, among which at least one includes antimicrobial functions, which is fundamental to ensure the user's health and well-being.

In addition to contributing positively to the environment, the reusability of said lining guarantees the disclosed lining is an economical and hygienic solution for the user.

The breathability of the multilayer lining for clothing is advantageous to maintain the user's temperature stability and comfort during its use. Moreover, the lining has an antimicrobial function that will last for up to 60 washes in a washing machine. To preserve its antimicrobial feature after several washes, the lining may be sanitized without softener or bleach, as to retain its functions.

The US patent application US 20130066288 discloses several embodiments of multilayer linings for clothing. One of these embodiments discloses a lining integrating a first layer with absorbing and draining functions; a second antimicrobial layer; a third waterproof and breathable layer made up of polytetrafluoroethylene (PTFE); a fourth outer layer of fabric, which protects the third layer and helps to diffuse moisture, and a fifth layer of outer finish.

It is worth mentioning that the waterproof layer of the present patent application is composed of breathable thermoplastic polyurethane (TPU), while the breathable layer of the US application in question is made of PTFE. The use of TPU in the waterproof layer provides benefits to the multilayer lining of this disclosure, since it is breathable and promotes vapor dispersion and waterproofing. In addition to all this, the TPU layer used in the claimed multilayer lining is added to the lining without using any chemical treatment, turning it into a cheaper option, of rapid production and even more hygienic, mainly for users with allergic problems, for example. In view of the foregoing features, the multilayer lining of the present disclosure is a technical solution that differs from the one described on the aforementioned US patent document.

BRIEF DESCRIPTION OF THE DISCLOSURE

The present disclosure provides a breathable, reusable and leakproof multilayer lining for clothing. A purpose of this lining is to avoid the release of body fluids such as sweat, blood, vaginal fluids, menstrual fluid, urine, breast milk or postoperative fluids. Additionally, said multilayer lining for clothes has absorbing, antimicrobial, waterproofing and vapor dispersion functions.

The multilayer lining for clothing may be sewn or pasted to the garment in question, including but not limited to: men and women's underwear, shorts, Bermuda shorts, skirts, trousers, brassieres, shirts, t-shirts, overalls, panty girdles, dresses, women's and men's pajamas, and others.

BRIEF DESCRIPTION OF THE FIGURES

The following is a description of the present disclosure according to the various embodiments depicted in the figures.

DETAILED DESCRIPTION OF THE DISCLOSURE

Figure 1:
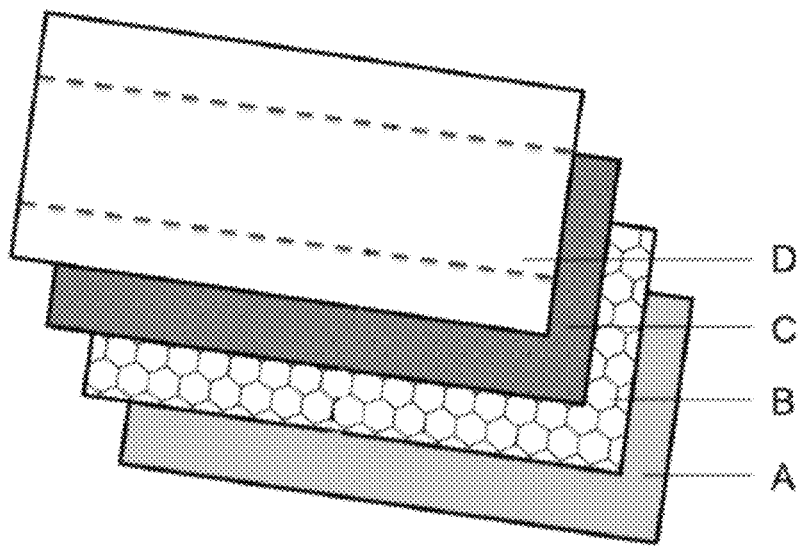
FIG. 1 is a schematic view showing the multilayer lining for clothing composed by layers A, B, C and D.
Figure 2:
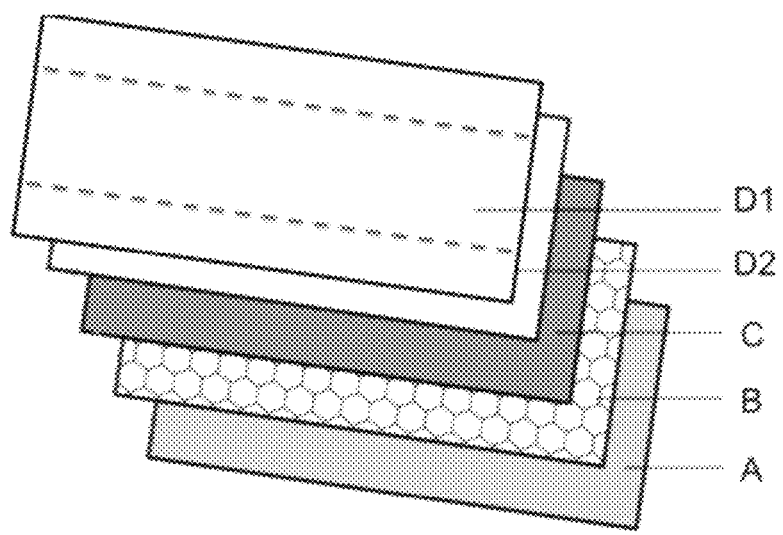
FIG. 2 is a schematic view showing the multilayer lining for clothing composed by layers A, B, C, D1 and D2.

The present disclosure provides a multilayer lining for clothing that may be used in garments, for example in men and women's underwear.

The multilayer lining for clothing has at least 4 (four) layers, wherein the first layer "A" is made of outer finish material, selected from the group including: cotton, modal, bamboo, viscose, polyester, microfiber, nylon, including combinations with elastane, lycra and spandex.

A second layer "B" of a natural or synthetic material selected from a group including: cotton, polyester, bamboo, viscose, tinsel, modal and nylon with a weight between approximately 60 and 350 g/m2, and it may have a mesh structure with twisted fabric, fleece, plush or microfiber. This layer is chemically treated with an antimicrobial product, especially with products containing silver ions, such as Silpure (product by Thomson Research associates).

The third layer of the multilayer lining, layer "C", is composed of breathable thermoplastic polyurethane of approximately 0.015-0.020 mm, which is applied without using any harmful chemicals, such as those present in linings already known in the art.

A fourth inner layer, layer "D", is a contact layer made of any fabric with appropriate features for absorption, hygiene, draining, etc.

Layer "C", the third layer, is fixed to the second layer, layer "B", by a lamination process, with heat application. The rest of the layers are bonded through a specific sewing process.

The combination of waterproof layer "C" and antimicrobial layer "B" increases antimicrobial effectiveness due to the fact that layer "C" is located at the bottom of the multilayer lining, so that most of the absorbed liquid is not in contact with the antimicrobial fabric. In addition, the organization of layers "B" and "C" improves the flexibility of the garment when using the multilayer lining. Also, because of the layer layout, the lining of the present disclosure is not too thick, so its use becomes more comfortable for the user.

In another modality of the present disclosure, layer "D" is replaced by layers "D1" and "D2". Layer "D2" is an optional layer with an absorbing function, while layer "D1" is the inner layer.

Layer "D1" is the inner layer of the lining, which may be made of approximately 51% of the following materials: modal, viscose, bamboo, carbon or cotton with approximately 90-300 gsm. Additionally, layer "D1" may be knitted or weaved with a special pattern to be created as follows: (1) bigger openings or conduits for the liquid, wherein the said conduits facilitate the mechanical passage, through capillary absorption, to the next layer. This liquid includes, but is not limited to, liquids with high viscosity and/or less polarized than water, with (2) 3D texture providing a larger contact surface towards the body—allowing a faster drying and a drier touch if compared with Jersey fabric of simple or double mesh of comparable weight and denier.

Layer "D2" of the present disclosure is an absorbent layer made of at least approximately 90% polyester or microfiber with coolplus fiber, integrated with rapid absorption and drying technology as well as cooling properties with approximately 100-300 gsm. Coolplus fibers are different from technologies commonly used in clothing manufacture with rapid absorption and drying, since such technologies use chemicals that may fade after washing due to the fact that they were developed with rapid absorption and drying functions. Additionally, because coolplus fibers are directly added to the fabric, they are the most resistant ones, and they do not get damaged or loose over time. Such features help to regulate temperature, preventing it from increasing in the lining.

Depending on the purpose of the multilayer lining for clothing, this layer may be optional or present in larger quantities.

The multilayer lining for clothing may resist up to 60 washes in a washing machine, provided that due care is taken, may comply with IS20743 standard, and may stand a waterproofing test for up to 12 hours while applying 500 mL of fluid. It may also be pervious to air.

The skilled in the art will value the knowledge provided herein and will be able to reproduce the disclosed lining in the presented embodiments, as well as in other variations, included in the scope of the annexed claims.

The invention claimed is:

1. A multilayer lining for clothing, the multilayer lining consisting of:
    a first layer, a second layer, a third layer and a fourth layer,
    the first layer is an outer layer, the second layer is located between the first and the third layer, the third layer is located between the second layer and the fourth layer, the fourth layer is an inner layer, and the second layer and the third layer are located between the first layer and the fourth layer,
    the first layer comprises a layer of outer finish material,
    the fourth layer comprises an absorbent and drainable layer which is positioned to be in contact with skin of a user,
    the second layer comprises a layer of natural or synthetic material that is treated with an antimicrobial product, and
    the third layer comprises a waterproof layer of breathable thermoplastic polyurethane,
    wherein the second layer and the third layer are heat laminated to one another, and the first layer and the fourth layer are connected to one another via sewing, and
    the fourth layer contains a knitted or weaved pattern that includes a) conduits that facilitate mechanical passage of liquid, and b) a three-dimensional texture.

2. The multilayer lining for clothing according to claim 1, wherein the layer of outer finish material comprises a material that is selected from:
    cotton, modal, bamboo, viscose, polyester, microfiber, nylon, including combinations with elastane and spandex.

3. The multilayer lining for clothing according to claim 1, wherein the natural or synthetic material has a weight of between 60 and 350 g/m$^2$.

4. The multilayer lining for clothing according to claim 1, wherein the natural or synthetic material comprises a material that is selected from:
    cotton, polyester, bamboo, viscose, tinsel, modal and nylon.

5. The multilayer lining for clothing according to claim 1, wherein the natural or synthetic material comprises a structure that is selected from mesh, woven fabric, knitted fabric, fleece, plush or microfiber.

6. The multilayer lining for clothing according to claim 1, wherein the layer of natural or synthetic material is chemically treated with an antimicrobial product containing silver ions.

7. The multilayer lining for clothing according to claim 1, wherein the waterproof layer has a thickness of 0.015-0.020 mm.

8. The multilayer lining for clothing according to claim 1, wherein the fourth layer comprises a first sublayer and a second sublayer, the first sublayer is positioned inward from the second sublayer, and the second sublayer is positioned between the third layer and the first sublayer.

9. The multilayer lining for clothing according to claim 8, wherein the first sublayer is knitted or weaved and comprises up of 51% modal, viscose, bamboo, carbon or cotton, and the first sublayer has a weight between 90 and 300 g/m$^2$.

10. The multilayer lining for clothing according to claim 8, wherein the second sublayer comprises at least 90% polyester or microfiber with a fabric with a permanent wicking function, and the second sublayer has a weight between 100 and 300 g/m$^2$.

* * * * *